(12) United States Patent
Lastinger et al.

(10) Patent No.: US 10,330,623 B1
(45) Date of Patent: *Jun. 25, 2019

(54) SYSTEMS AND METHODS FOR DETECTING A LIQUID

(71) Applicant: Helvetia Wireless LLC, Scottsdale, AZ (US)

(72) Inventors: Roc Lastinger, Cave Creek, AZ (US); Brian C. Woodbury, Gilbert, AZ (US)

(73) Assignee: Helvetia Wireless LLC, Scottsdale, AZ (US)

( * ) Notice: Subject to any disclaimer, the term of this patent is extended or adjusted under 35 U.S.C. 154(b) by 44 days.

This patent is subject to a terminal disclaimer.

(21) Appl. No.: 15/715,472

(22) Filed: Sep. 26, 2017

Related U.S. Application Data

(63) Continuation of application No. 15/005,943, filed on Jan. 25, 2016, now Pat. No. 9,810,652, and a continuation of application No. 14/265,481, filed on Apr. 30, 2014, now Pat. No. 9,322,797.

(51) Int. Cl.
*G01N 27/07* (2006.01)

(52) U.S. Cl.
CPC .................... *G01N 27/07* (2013.01)

(58) Field of Classification Search
CPC ........ G01N 27/04; G01N 27/02; G01N 27/06; G01N 33/18; G01N 27/045
USPC ................. 324/693, 600, 649, 691
See application file for complete search history.

(56) References Cited

U.S. PATENT DOCUMENTS

| | | |
|---|---|---|
| 3,706,953 A | 12/1972 | Kicks |
| 4,319,232 A | 3/1982 | Westphal |
| 4,843,445 A * | 6/1989 | Stemme ............... G01F 1/6845 257/470 |
| 5,137,033 A | 8/1992 | Norton |
| 5,463,377 A | 10/1995 | Kronberg |
| 5,590,648 A | 1/1997 | Mitchell |
| 5,662,637 A | 9/1997 | Kitaoka |
| 5,665,082 A | 9/1997 | Boulnager |
| 6,348,640 B1 | 2/2002 | Navot |
| 6,559,772 B2 | 5/2003 | Zand |
| 6,774,800 B2 | 8/2004 | Friedman |
| 7,239,246 B2 | 7/2007 | Picco |
| 7,276,041 B2 | 10/2007 | Moll |
| 7,352,286 B2 | 4/2008 | Chan |
| 8,211,559 B1 * | 7/2012 | Waggoner ............. H01M 10/48 324/691 |

(Continued)

FOREIGN PATENT DOCUMENTS

| | | |
|---|---|---|
| EP | 1542635 | 6/2005 |
| EP | 1768551 | 10/2010 |

(Continued)

*Primary Examiner* — Giovanni Astacio-Oquendo
(74) *Attorney, Agent, or Firm* — Letham Law Firm LLC; Lawrence Letham

(57) ABSTRACT

Systems and methods for detecting a liquid. Detection a liquid may include detecting liquid at a boundary of an area and reporting the presence of the liquid. Reporting liquid at a boundary may prevent leaking of the liquid from the area. Detecting also includes detecting liquid inside the area. The amount of liquid detected inside the boundary may relate to a range of amounts of liquid. The minimum amount of the range may represent the minimum amount of liquid that is permissible in the area prior to taking action to deal with the liquid.

17 Claims, 8 Drawing Sheets

(56) References Cited

U.S. PATENT DOCUMENTS

| | | | |
|---|---|---|---|
| 8,421,636 B2 | 4/2013 | Collette | |
| 8,454,550 B2 | 6/2013 | Koenig | |
| 8,682,952 B2 | 3/2014 | Kutzik | |
| 2001/0044588 A1 | 11/2001 | Mault | |
| 2002/0021220 A1 | 2/2002 | Dreyer | |
| 2004/0220538 A1 | 11/2004 | Panopoulos | |
| 2006/0178616 A1 | 8/2006 | Hartman | |
| 2009/0212918 A1 | 8/2009 | Bandy | |
| 2009/0243833 A1 | 10/2009 | Huang | |
| 2010/0015438 A1* | 1/2010 | Williams | C23C 16/006 428/332 |
| 2010/0267161 A1* | 10/2010 | Wu | C12Q 1/001 436/149 |
| 2011/0095884 A1 | 4/2011 | Xu | |
| 2011/0172625 A1 | 7/2011 | Wada | |
| 2011/0176563 A1* | 7/2011 | Friel | C30B 25/02 372/3 |
| 2013/0053754 A1 | 2/2013 | Heppe | |
| 2013/0110064 A1 | 5/2013 | Richardson | |
| 2014/0039351 A1 | 2/2014 | Mix | |
| 2015/0299894 A1* | 10/2015 | Markham | C30B 29/04 250/458.1 |

FOREIGN PATENT DOCUMENTS

| | | |
|---|---|---|
| WO | 2001033528 | 5/2001 |
| WO | 2002015141 | 2/2002 |
| WO | 2004034929 | 4/2004 |
| WO | 2008021206 | 2/2008 |
| WO | 2008115987 | 9/2008 |
| WO | 2010123425 | 10/2010 |
| WO | 2011025549 | 3/2011 |
| WO | 2012102608 | 8/2012 |
| WO | 2013097899 | 7/2013 |
| WO | 2013155199 | 10/2013 |
| WO | 2014165041 | 10/2014 |

* cited by examiner

SYSTEMS AND METHODS FOR DETECTING A LIQUID

FIELD OF THE INVENTION

Embodiments of the present invention relate to systems and methods for detecting a liquid (e.g., moisture, wetness).

BACKGROUND OF THE INVENTION

Detecting the presence of liquid may include using a system to detect the liquid. In an application where the system detects liquid in an area, a user may benefit from a system that detects the exit of the liquid from the area or the presence of a liquid within the area.

BRIEF DESCRIPTION OF THE DRAWING

Embodiments of the present invention will now be further described with reference to the drawing, wherein like designations denote like elements, and.

DETAILED DESCRIPTION OF THE PREFERRED EMBODIMENTS

Figure 1:
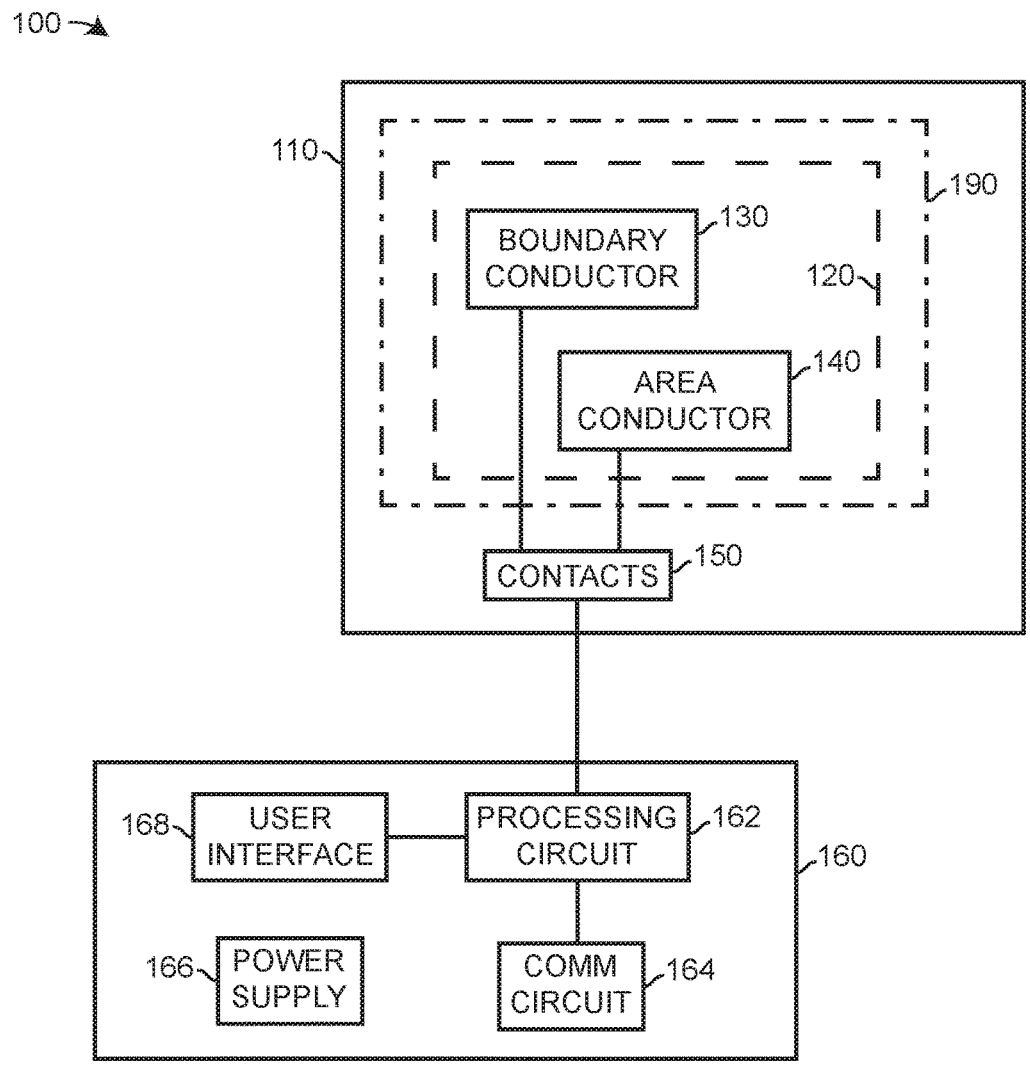
FIG. 1 is a functional block diagram of a system for detecting a liquid according to various aspects of the present invention.

A system for detecting liquid may include conductors and a determiner. A system may detect a liquid (e.g., moisture, wetness). A system may detect an amount of liquid. A system may detect a physical property, a physical quantity, and/or a chemical property to detect a liquid. A system may detect a change in a physical property, a physical quantity, and/or a chemical property to detect a liquid.

A physical property may include concentration, electric charge, electrical conductivity, electrical impedance, electric potential, inductance, resistivity, and frequency. A chemical property may include PH, composition of the liquid, reactivity, and electromotive force.

A system may detect a liquid in an area. A system may detect whether a liquid is exiting (e.g., leaking, leaving) from an area. The conductors of a system, or a portion thereof, may be positioned in an area for detecting a liquid in the area. A portion of the conductors of a system may be positioned at or proximate to an outer boundary of an area to detect whether a liquid is exiting the area. An area may include any two-dimensional area or three-dimensional volume. An area may be vacant of any material other than air and/or contain a material. A material in an area may absorb a liquid. The conductors of a system, or a portion thereof, may contact (e.g., touch) a material in an area to detect a liquid in the area. A boundary of an area may include an outer edge of the area. A boundary may include an outer edge of an absorbent layer positioned in the area.

A system may provide (e.g., exert, deliver, apply) a force (e.g., mechanical, electrical, magnetic) to detect a liquid. A system may provide a force to an area, or a portion thereof, to detect a liquid in the area. A system may provide a force to a material in the area to detect a liquid in the material of the area. The force applied by the system to an area may cooperate with the physical and/or chemical properties of the material and/or a liquid in the area to detect the liquid.

A system may measure (e.g., detect), deduce, and/or calculate a physical property made manifest by application of the force to detect a liquid. A system may detect a physical property of a material in the area to determine a liquid or absence thereof in the area. A force applied by a system to detect a liquid may include an electric force. For example, a system may include conductors that are positioned in an area. A system may apply a voltage to two or more conductors to detect a liquid.

A material in an area may have an impedance. A magnitude of an impedance of a material absent a liquid may be different than the magnitude of the impedance of the material when the material contains (e.g., holds) an amount of liquid. An impedance of a material may be inversely proportional to an amount of liquid in the material. For example, when a material is dry (e.g., absent liquid, not damp) an impedance of the material may be high. A high impedance of a material may impede current flow through the material. Current flow through a material that is dry may be negligible or zero. Low current flow through a material that is dry may be equivalent to an open circuit.

When a material is damp (e.g., wet, contains a liquid), the impedance of the material may decrease. The impedance of a material that contains a liquid may be proportional to impedance of the liquid and/or the amount of the liquid in the material. The impedance of a material that contains a liquid may be inversely proportional to an amount of the liquid in the material. As the amount of liquid increases per unit volume of the material, the impedance of the material may decrease. As the impedance of a material decreases, a current may flow through the material and/or the liquid in the material. The flow of a current through the material and/or liquid in the material may be equivalent to a closed circuit. An area in a material that permits the flow of a current may be referred to as an electrical circuit. An electrical circuit, or an area of reduced impedance, may permit current to flow from one portion of an area to another portion of the area.

The magnitude of the impedance through a conductive liquid depends on the distance between electrical probes positioned in the liquid. As the distance between the probes increases, the amount of liquid between the probes increases, therefore the impedance between the probes increases. The conductors of conductors 120 perform the function of an electrical probe in a conductive liquid so that the impedance of the liquid between any two conductors is proportional to the distance between the conductors. As used herein, the term "liquid" means a conductive liquid.

Conductors may be positioned proximate to or in a material. Conductors may be spaced apart in the material. When the material is substantially dry, little or no current may flow between the conductors in the material. When little or no current flows between conductors via the material, an open circuit exits between the conductors. When the material is wet, some current may flow between conductors. As the amount of liquid increases in the material, the amount of current that flows between conductors may increase because the impedance between the conductors decreases. When the amount of current that flows between conductors reaches a threshold, an electrical circuit (e.g., closed circuit) exits between the conductors.

A method for detecting a liquid in an area may further provide information regarding the extent (e.g., distance, length) of the spread of the liquid in the area. A system that detects a liquid in a material having known physical properties may further determine an approximate volume (e.g., amount, quantity) of the liquid in the area.

An area may include a boundary. An outer boundary of an area includes a portion of the area where the area ends. The outer boundary of an area that includes a material may be the location where the material ends or the edge of the material. A system may detect liquid at a boundary of an area. Detecting a liquid at a boundary of an area may be an indication (e.g., evidence, indicia) that the liquid is leaving (e.g., exiting, leaking from) the area.

A user of a system for detecting liquid may assign a different importance to detecting liquid at a boundary of an area as opposed to detecting liquid that is within the boundary of the area. For example, a system may detect liquid in a medical pad that is placed on a patient's bed. Health care standards may permit a certain amount of liquid to be absorbed by the pad, but a pad must be immediately changed it liquid leaks from the pad or a leak is imminent. The same standard may apply to a diaper in that it should be immediately change if it starts leaking or may soon leak. A user may desire a system that provides notice of a minimum amount of liquid within an area and notice when the liquid is at a boundary of the area.

For example, system 100, shown in FIG. 1, may include conductors 120 positioned in area 110 and determiner 160. Conductors 120 may include boundary conductors 130 for detecting a liquid proximate to boundary 190. Conductors 120 may include area conductors 140 for detecting a liquid within boundary 190. Conductors 120 may include contacts 150 for facilitating an electrical, mechanical, and/or physical connection to boundary conductors 130 and/or area conductors 140. Conductors may be positioned at any location in an area. Conductors may be positioned in and/or on a material in an area. Two examples of conductors positioned in a material in an area are provided in FIGS. 2 and 3. Various implementations of conductors (e.g., 400, 500, 600, 700, 800, 900) are provided in FIGS. 4-8.

Determiner 160 may include processing circuit 162, communication (e.g., comm) circuit 164, power supply 166, and/or user interface 168. In one implementation, determiner 160 includes only processing circuit 162 that includes a circuit for determining whether a liquid is present in an area. A device for receiving information (e.g., reader) from processing circuit 162 may provide power to processing circuit 162 for performing the operation of determining whether liquid is present. In another implementation determiner 160 includes processing circuit 162 and power supply 166. A device for receiving information from processing circuit 162 may include a communication circuit for communicating the information to other devices.

A conductor may be formed of any material capable of conducting an electrical current, such as copper, aluminum, gold, silver, semiconductor material, and carbon. A conductor may be formed in any conventional manner. A conductor may include conductive material in the form of a wire, conductive material deposited onto another material, and/or conductive ink printed on a surface. A conductor may be formed to have any shape (e.g., width, length) whether uniform or varying. A conductor may carry (e.g., transport) a current at a voltage. A conductor may have an impedance. The impedance of the conductor may be related to the material that forms the conductor, an amount of material that forms the conductor, the shape of the conductor, and a cross-sectional area of the material that forms the conductor. The conductance of a conductive material formed as a trace may be proportional to the number or squares of material that form the trace.

A power supply includes a supply of energy. Energy may be used for enabling the operation of electronic circuits (e.g., devices) such as a processing circuit, a user interface, and/or a communication circuit. A power supply may include any conventional component for providing energy such as a battery, a transformer that transforms line power, and/or a capacitor. A power supply may store energy for providing. In the case where a determiner is implemented using passive RF technology (e.g., RFID tag), a power supply may include a coil for transforming (e.g., converting) transmitted electromagnetic waves from an RF reader into electrical energy. Energy from a power supply may be used as a force for detecting a liquid as discussed above.

A communication (e.g., comm) circuit may provide (e.g., transmit) and/or receive information (e.g., data). A communication circuit may transmit and/or receive (e.g., communicate) information via a wireless link and/or a wired connection. A communication circuit may communicate using any conventional protocol for wireless (e.g., radio, light, sound, vibrations) and/or wired (e.g., electrical, optical) mediums. A communication circuit may receive information from a processing circuit for transmission. A communication circuit may provide received information to a processing circuit.

A user interface may include electronic devices (e.g., switches, push buttons, touch screen, Bluetooth transceiver) for receiving information (e.g., data) from a user. A user may manually manipulate one or more electronic devices of a user interface to provide information. Electronic devices for receiving information from a user may include a wireless receiver that receives information from an electronic device (e.g., smart phone, table, watch, pager). A user may manually provide information to a user interface via a electronic device. A user interface may include electronic devices for providing information to a user. A user may receive visual and/or auditory information from a user interface. A user may receive visual information via devices (e.g., LCD screen, LEDs) that display information. A user interface may include a wireless transmitter for transmitting information to an electronic device for presentation to a user.

A user interface may receive information for providing to a user from a processing circuit, a communication circuit, and/or a power supply. Information may include status of the power supply, information communicated via the communication circuit, notice of detected liquid, and location of detected liquid. Information received by a user interface from a user may be provided to a power supply, a processing circuit, and/or a communication circuit. Information from a user may instructions (e.g., information) for controlling an operation of the determiner. Information from a user may include communication parameters for a communication circuit, information regarding an area, information regarding a material in an area, an amount of force (e.g., voltage) to apply to detect a liquid, a frequency of applying a force to detect a liquid, and an instruction to reset operations. Information from a user may be used by a processing circuit to control the operation of a system for detecting liquid.

A communication circuit in combination with an electronic device (e.g., smart phone, tablet) may perform the functions of a user interface so that user interface 168 may be omitted.

A processing circuit includes any conventional circuit. A processing circuit may include passive electronic devices (e.g., resistors, capacitors, inductors) and/or active electronic devices (op amps, comparator, analog-to-digital converter, digital-to-analog converter, microprocessors, programmable logic, semi-conductor memory). A processing circuit includes any conventional circuit that provides and/or receives an electrical signal whether digital and/or analog in nature. A processing circuit may include conventional data buses, analog-to-digital converters, output ports, input ports, timers, logic circuits, memory, and arithmetic units. A processing circuit may include any conventional microcontroller, microprocessor, signal processor, logic circuits, and/or programmable logic. A processing circuit may store information (e.g., data). A processing circuit may manipulate data.

A processing circuit may apply a force to detect a liquid. A processing circuit may detect a physical property and/or a change in a physical property to detect a liquid. A processing circuit may provide a current and/or voltage (e.g., signal) via an output port to detect a liquid. A processing circuit may provide a signal in accordance with an interval. A processing circuit may detect a signal via an input port to detect a physical property and/or a change in a physical property. A processing circuit may measure a characteristic (e.g., magnitude, duration) of a signal via an input port. A processing circuit may apply a force, detect (e.g., measure) a physical characteristic, and perform a calculation using the detected physical characteristics.

A processing circuit may store measured (e.g., detected) data, perform calculations using measured data whether presently detected or previously detected and stored, transform detected data from one form to another, and provide a notice responsive to a result of an operation.

An input and/or output port of a processing circuit may electrically couple to one or more conductor of conductors 120. A processing circuit may apply a force to conductors 120. A processing circuit may measure a response of conductors 120 to a force applied to conductors 120. A processing circuit may store information regarding the characteristics of the conductors of conductors 120. A processing circuit may use stored information regarding the characteristics of the conductors of conductors 120 to detect a liquid in an area. A processing circuit may apply a force to selected conductors of conductors 120. A processing circuit may use information measured from conductors 120 to perform an operation. Operations responsive to information measured from conductors 120 may include further and/or different measurements, application of an additional force, and providing a notice.

In an implementation, determiner 160 includes a conventional microcontroller with input and output ports and at least one data bus for communicating with communication circuit 164. Processing circuit 162 electrically couples to boundary conductors 130 and/or area conductors 140 via contacts 150. Power supply 166 includes a conventional battery.

Figure 2:
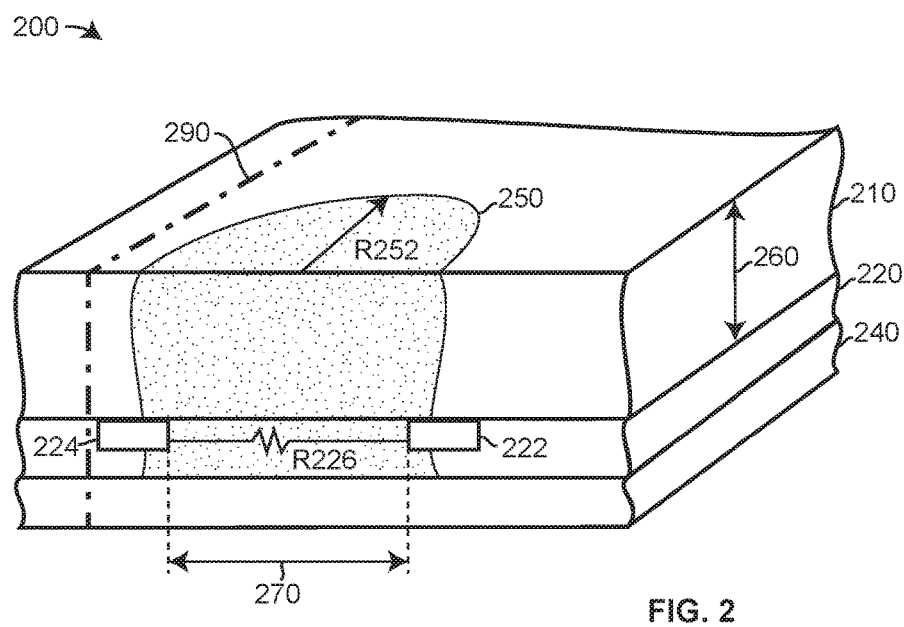
FIGS. 2 and 3 are cross-sections of areas that include conductors for detecting a liquid.

In area 200 of FIG. 2, processing circuit 162 electrically couples to boundary conductors 222 and 224. In area 300 of FIG. 3, processing circuit 162 electrically couples to area conductors 322 and 324. Conductors 222 and 224 and/or conductors 322 and 324 may be implemented as conductive traces printed onto absorbent layer 210. Conductors 222 and 224 are positioned proximate to boundary 290 of area 200 which is proximate to the edge of absorbent layer 210 and/or substrate 240. Conductors 322 and 324 are not proximate to boundary 290 or any other boundary of area 300, but are positioned within area 300 away the boundary.

Conductors in an area may be positioned above an absorbent layer and/or below an absorbent layer. Boundary conductors 130 and/or area conductors 140 may be positioned above and/or below an absorbent layer. Boundary conductors 130 may be positioned on a same side and/or different sides of an absorbent layer. Area conductors 140 may be positioned on a same side and/or different sides of an absorbent layer. Boundary conductors 130 may be positioned on a same side and/or a different side of an absorbent layer as area conductors 140.

Substrate 240 is formed of a non-permeable (e.g., non-absorbent) material that is positioned proximate a surface and/or object that is to be protected from the liquid. A surface may include any surface (e.g., wood, metal, tile). An object may include any object (e.g., furniture, electronic devices). Substrate 240 stops the movement of liquid from absorbent layer 210 to the surface and/or object. Substrate 240 is formed of a material that is an electrical insulator so that a circuit cannot form between conductors 222 and 224 or conductors 322 and 324 through substrate 240. Conductors may be positioned (e.g., printed) on a substrate. Absent an absorbent layer, liquid may spread across a substrate to establish an electrical circuit between conductors on the substrate.

A substrate need not be limited to a planar (e.g., flat) contour. A substrate may have edges near a boundary of the substrate that are elevated above the area (e.g., center) of the substrate so that a liquid may accumulate in the lower elevations of the substrate before over flowing. Absent an absorbent layer, area conductors 140 on the substrate may detect a liquid when only a small amount of liquid is on the substrate. As the liquid accumulates on the substrate the level of the liquid may rise until it establishes an electrical circuit between boundary conductors 130 near the boundary of the substrate.

A substrate may be formed of two or more layers of the same and/or different materials.

To detect liquid, processing circuit 162 applies a voltage (e.g., force) to conductors 222 and 224 or conductors 322 and 324 and measures a current and/or a voltage that results from the application of the voltage. Absorbent layer 210 is formed of a material with a low conductivity (e.g., high impedance) when dry so that little or no current flows between conductor 222 and 224 or conductors 322 and 324 when absorbent layer 210 contains little or no liquid. Because little or no current flows between conductors 222 and 224 or conductors 322 and 324 when absorbent layer 210 contains little or no liquid, processing circuit 162 cannot detect an electrical circuit (e.g., open circuit) between conductors 222 and 224 or conductors 322 and 324.

When liquid 250 or 350 is present in absorbent layer 210, the impedance of absorbent layer 210 is reduced from a very high impedance, possibly close to infinite (e.g., open circuit), to a lower impedance that permits a current to flow between conductors 222 and 224 or conductors 322 and 324 via liquid 250 or 250 respectively. Processing circuit 162 may detect a threshold current and/or voltage between conductors to determine whether an electrical circuit exists between conductors. If the magnitude of the current between conductors is greater than a threshold or the magnitude of the voltage drop between conductors is less than a threshold, processing circuit 162 may determine that an electrical circuit exists between conductors.

An electrical circuit may develop between two conductors due to a reduced magnitude of the impedance between conductors. The impedance may be reduced by introducing a liquid having a low impedance and/or a high conductivity into the material. For example, the impedance of urine ranges from 10 ohms to 100 ohms per unit volume. The impedance of blood ranges from 300 to 550 ohms per unit volume. The impedance of liquids such as urine and/or blood is inversely proportional to the amount of salts in the liquid. The liquid in the absorbent material acts to decrease the impedance of the material in the area of the liquid. A reduced magnitude of impedance in an area between conductors permits a current to flow between the conductors. A threshold current flowing and/or voltage between conductors may be used to specify that a circuit exists between the conductors.

Processing circuit 162 may determine that an electrical circuit exits between conductors whenever a current or a voltage travels between two conductors without calculating a magnitude of an impedance between the conductors. In another implementation, processing circuit 162 may determine the magnitude of the impedance between conductors in order to determine the chemical composition of the liquid (e.g., urine, blood) in the area. A processing circuit may use information that relates impedance to chemical composition to provide a notice of detected liquid that includes information as to the possible composition of the liquid. Impedance information that relates impedance to chemical composition may be further related to the material that forms absorbent layer 210 and any possible interaction the liquid may have with the absorbent layer.

Upon detecting an electrical circuit and/or impedance below a threshold (e.g., reduced impedance) between two conductors (e.g., 222/224, 322/324), processing circuit 162 performs a function related to detecting a liquid. When processing circuit 162 detects an electrical circuit between conductor 222 and conductor 224, processing circuit 162 performs a function of reporting that a liquid had been detected. Processing circuit 162 may further report that the liquid is proximate to a boundary, in this case boundary 290, or crossing a boundary of area 200. When processing circuit 162 detects an electrical circuit between conductor 322 and conductor 324, processing circuit 162 performs a function of reporting that a liquid has been detected. Processing circuit 162 may further report that the liquid is not proximate to a boundary, but that is located (e.g., positioned) within area 300. The notices may be communicated to a user via communication circuit 164, via an audible indicator of user interface 168, and/or via a visual indicator of user interface 168.

In accordance with a distance between two conductors, processing circuit 162 may determine a spread and possibly a minimum volume of the liquid in an area. Conductors may have a spacing between each other that is known or detectable to processing circuit 162. The existence of a circuit between two conductors indicates that a liquid has spread between the two conductors. A processing circuit that has information regarding the spacing of conductors may determine the spread of the liquid due to the existence of a circuit. A liquid may have a known impedance per unit area or unit volume. A processing circuit may determine the impedance through a liquid and use information regarding the impedance of the liquid to determine the spread and/or concentration of the liquid.

For example, upon detecting a circuit between conductors 222 and 224, processing circuit 162 may use stored information to determine that the spacing between conductors 222 and 224 is a distance 270. Processing circuit 162 may use stored information to determine that the distance between conductors 322 and 324 is distance 370. Knowing the distance between two conductors that have an electrical circuit between each other provides processing circuit 162 the information that the liquid has spread at least the distance that separates the conductors. Assuming uniform absorption of the liquid in the absorbent material, the distance between conductors infers an area of liquid spread. Accordingly, detecting an electrical circuit provides information as to a minimum area that the liquid had spread. For example, the area that a liquid has spread may be inferred by assuming a substantially circular spread of the liquid, so that the area of the spread between conductors 222 and 224 is the area of the circle represented by radius R252. The area of the spread between conductors 322 and 324 is the circular area represented by radius R352.

Information regarding the absorptive characteristics of the absorbent layer may be used to infer a volume from the area of spread of the liquid. At a minimum, the thickness 260 of absorbent layer 210 may be used with the area of spread to calculate a possible volume of detected liquid. Processor 162 may further have information as to any change in thickness of absorbent layer 210 as it absorbs liquid to aid in determining a possible volume of detected liquid.

An absorbent layer may be formed of one or more layers of the same material and/or different materials. For example, an absorbent layer may be formed of a highly absorbent material and a material that wicks moisture away from an object placed on the absorbent layer. The layer that wicks moisture transfers moisture from the object into the highly absorbent material to be absorbed. A layer that wicks moisture may include a material that enables the passage of liquid in a single direction. For example, a wicking layer may permit passage of liquid to an absorbent layer, but inhibit movement of the liquid out of the absorbent layer. An object that may be placed on top of an absorbent layer may include a human or animal.

The magnitude of the impedance between two conductors may provide further information as to the volume of a liquid between two conductors. Impedance R226 represents a reduced impedance between conductors 222 and 224 due to the presence of liquid 250. As discussed above a threshold value of the magnitude of impedance R226 may be used to indicate that an electrical circuit exists between conductors 222 and 224. Rather than determining only that impedance R226 is less than a threshold, processing circuit 162 may perform measurements to determine a value of the magnitude of the impedance of R226. Processing circuit 162 may use the value of the magnitude of impedance R226 to determine whether absorbent layer 210 is lightly damp, moderately damp, and/or saturated. Processing circuit 162 may use the value of the impedance to infer varying and/or increasing minimum volumes of liquid between conductors 222 and 224.

The same type of measurements and inference may be used to determine a minimum volume of liquid 360 between conductors 322 and 324 in accordance with the magnitude of impedance R336, distance 370, and thickness 260 of absorbent layer 210.

Although boundary 290 is drawn to the left, referring to FIG. 2, of conductors 222 and 224, boundary 290 may be drawn between conductors 222 and 224 or even to the right of conductor 222. Two conductors proximate to a boundary may detect liquid at the boundary. Two conductors may be positioned with respect to a boundary of an area to detect when a liquid may exit the area. Liquid crossing a boundary and/or exiting an area may result in undesirable consequences. An electric circuit between the conductors positioned proximate to a boundary indicates that a liquid is between the conductors and at the boundary. Depending on the position of the boundary with the edge of the area, liquid at the boundary may indicate that a leak is imminent.

In accordance with system for detecting liquid discussed above, conductors may be placed in an area to detect a liquid in the area away from a boundary and detect a liquid at a boundary. Using information related to conductor spacing, conductor location, characteristics of the absorbent material, and characteristics of liquids that may be present, a processing circuit may infer an area of spread of a liquid, a volume of a liquid, a chemical composition of a liquid, and/or a magnitude of saturation of an absorbent layer. Implementations 400, 500, 600, 700, 800, and 900 of conductors 120 are discussed below.

Implementations 400, 500, and 600 include conductor 470 and conductor 480. Portions of conductors 470 and 480 are positioned along boundary 410 of area 438. Along the boundary, conductors 470 and 480 are positioned distance 450 away from each other. In one implementation, conductors 470 and 480 are positioned at most distance 450 away from each other along boundary 410. Distance 450 may relate to the absorbency of an absorbent layer in area 438. Distance 450 may be proportional to the absorbency of the absorbent layer in the area. Distance 450 may be greater for absorbent layers that are highly absorbent where liquid moves less quickly beyond the boundary to create a leak. Distance 450 may be less for absorbent layers that are less absorbent where a liquid may spread more rapidly past boundary 410 to exit area 438 to leak. Although the distance between conductors 470 and 480 is shown as distance 450 along the entire boundary 410, the distance between conductors 470 and 480 may be different along one or more portions of boundary 410.

The volume of a liquid detected along boundary 410 may include a range of volumes of liquid. The volume of a liquid along boundary 410 is in accordance with the range of spread and the absorbent characteristics of the material along boundary 410. A highly absorbent material may result in a larger volume of liquid along boundary 410 before it is detected than a less absorbent material.

The distance between conductors 470 and 480 within boundary 410 is distance 460. In one implementation, the distance between conductors 470 and 480 within boundary 410 is at least (i.e., no less than) distance 460. Distance 460 may be greater than distance 450 because a liquid may spread inside boundary 410 without resulting in a leak. Inside the boundary, distance 460 between conductors 470 and 480 permits a liquid to spread within a range before the liquid is detected. The volume of a liquid detected inside boundary 410 may include a range of volumes of liquid. The volume of a liquid inside boundary 410 is in accordance with the range of spread and the absorbent characteristics of the material within boundary 410. A highly absorbent material may result in a larger volume of liquid inside boundary 610 before it is detected than a less absorbent material.

Because distance 460 is greater than distance 450, the volume of liquid within boundary 410 is greater than the volume of liquid along boundary 410 before the liquid is detected assuming that the absorbent layer along boundary 410 is similar to the absorbent material within boundary 410.

To detect a liquid, processing circuit 162 applies a voltage between conductors 470 and 480 to determine whether an electrical circuit exits between conductors 470 and 480. As discussed above, when little or no liquid is present, the impedance between conductors 470 and 480 is very high or possibly infinite. As a liquid spreads between conductors 470 and 480, whether or not an absorbent layer is present, the impedance between conductors 470 and 480 decreases. When the magnitude of the impedance is at or below a threshold, an electrical circuit between conductors 470 and 480 exists.

Within the boundary, the range of the spread of the liquid is represented by the diameter of liquids 430 and 434. Depending on where the liquid is introduced in the area (e.g., 432, 436), a liquid may spread a distance of 460 (e.g., liquid 430) before the liquid spreads between conductors 470 and 480 or up to a distance of about two times distance 460 (e.g., liquid 434) before the liquid contacts conductors 470 and 480 thereby creating a circuit.

Figure 3:
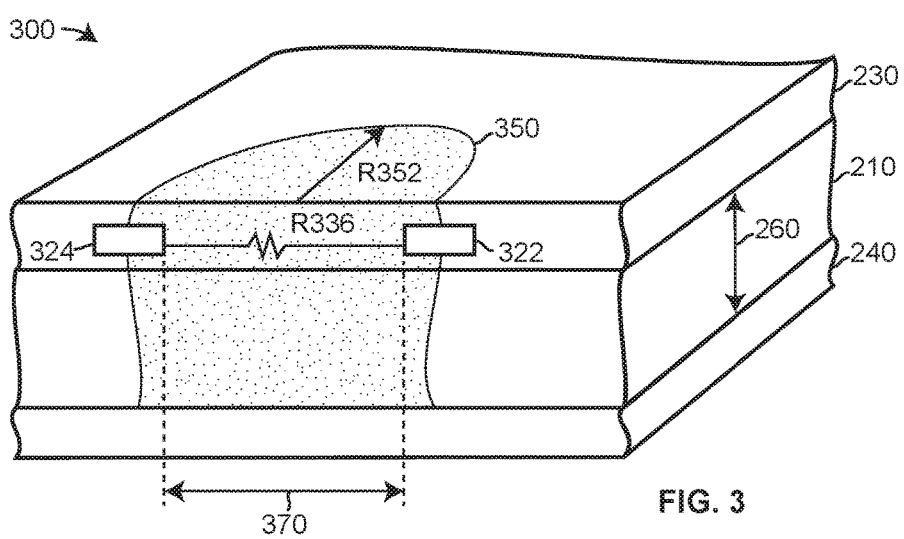
Figure 4:
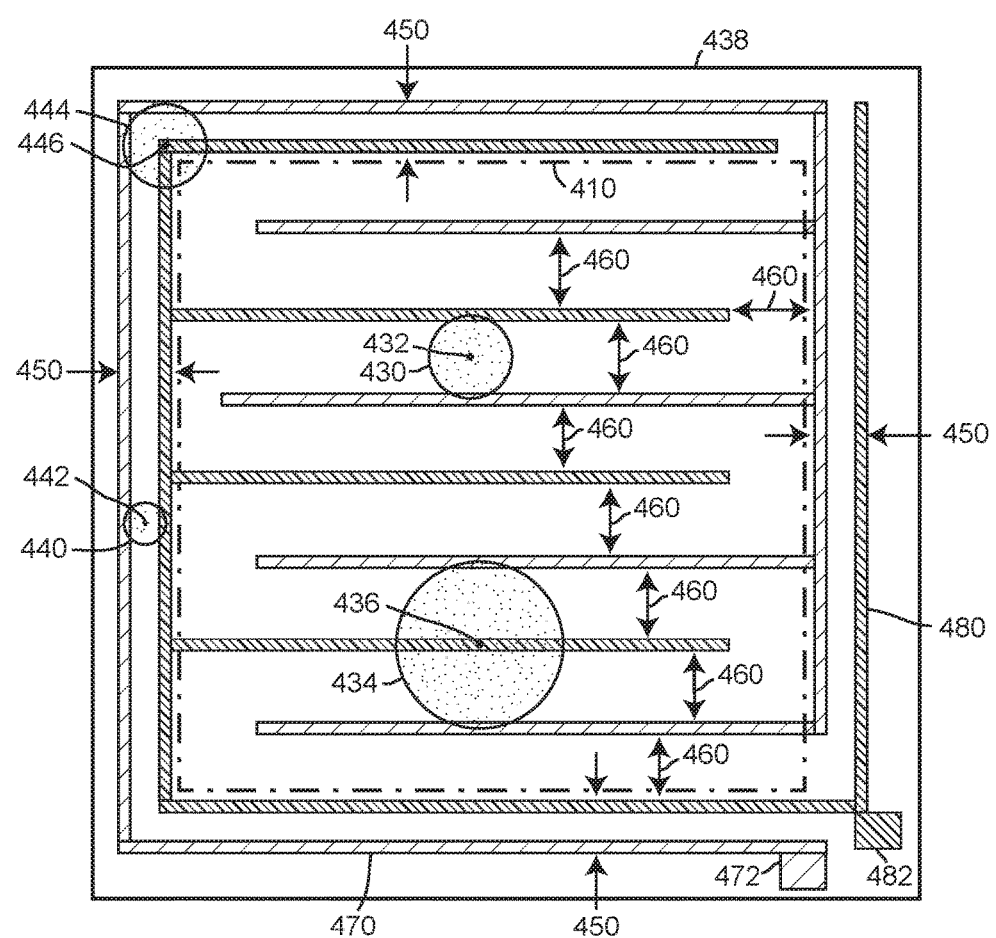
FIGS. 4-9 are implementations of the conductors of FIG. 1.
Figure 5:
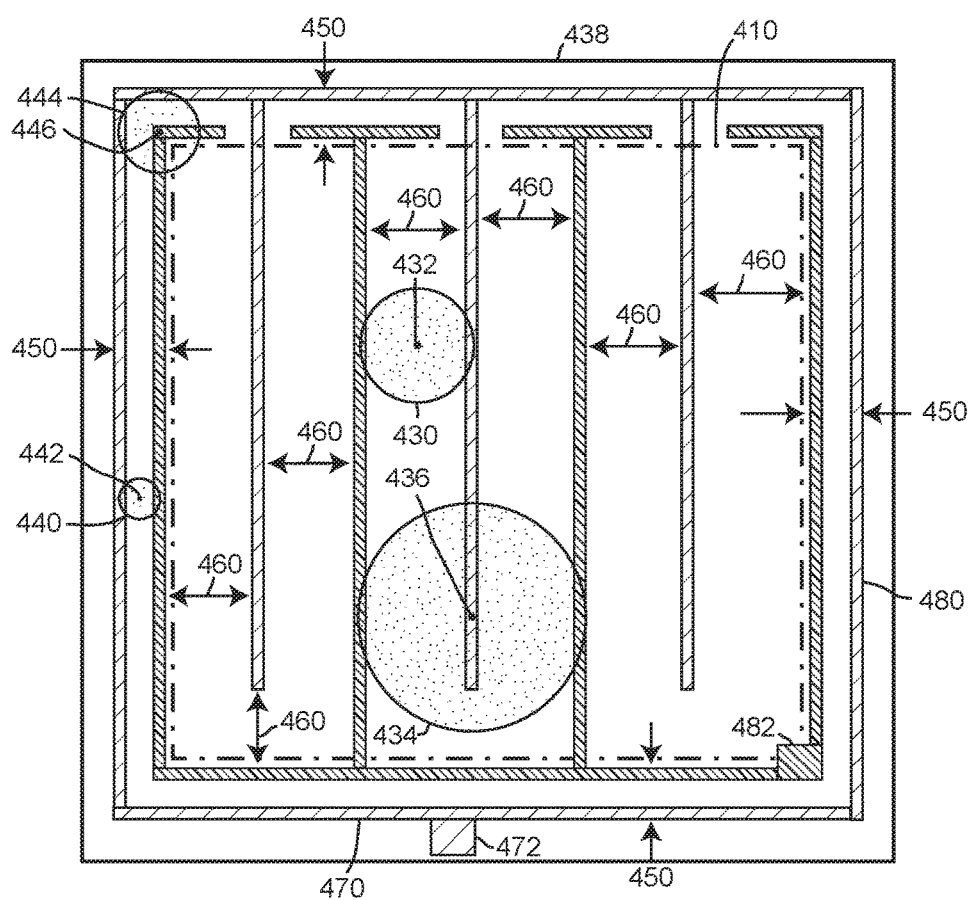
Figure 6:
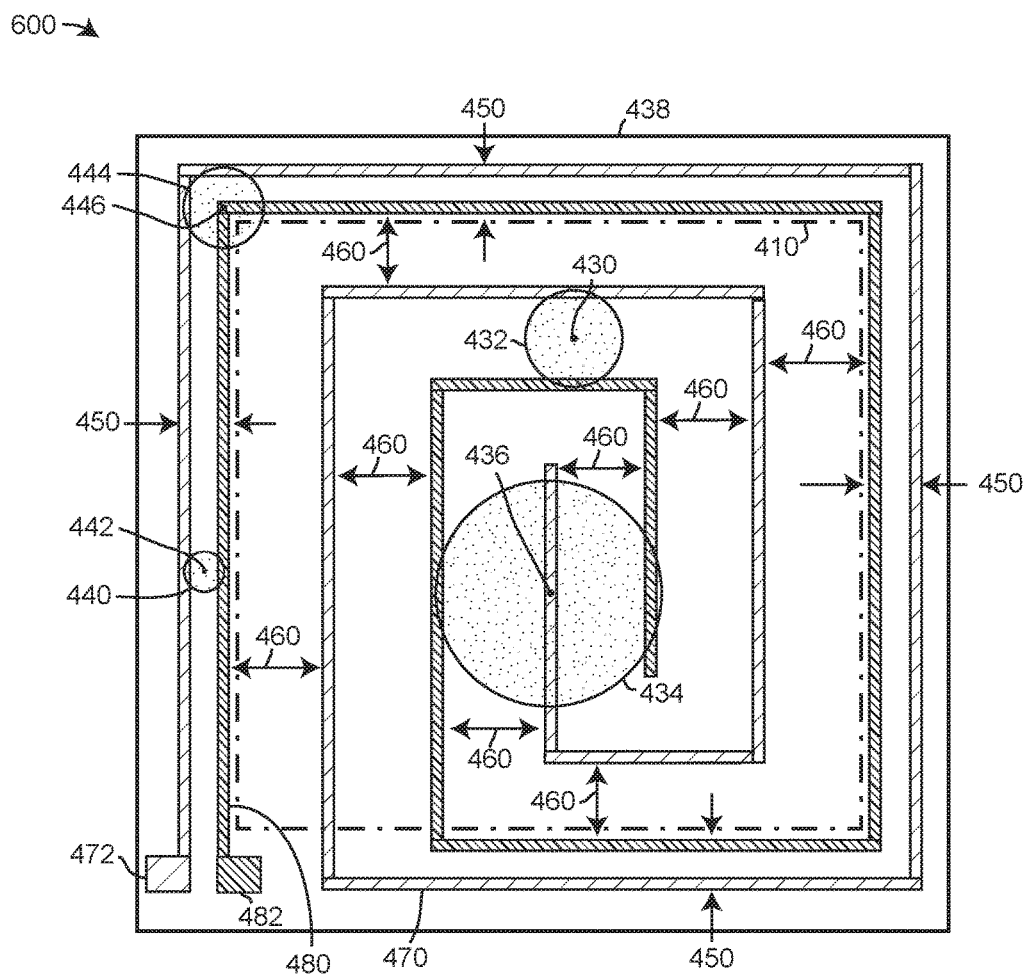
Figure 7:
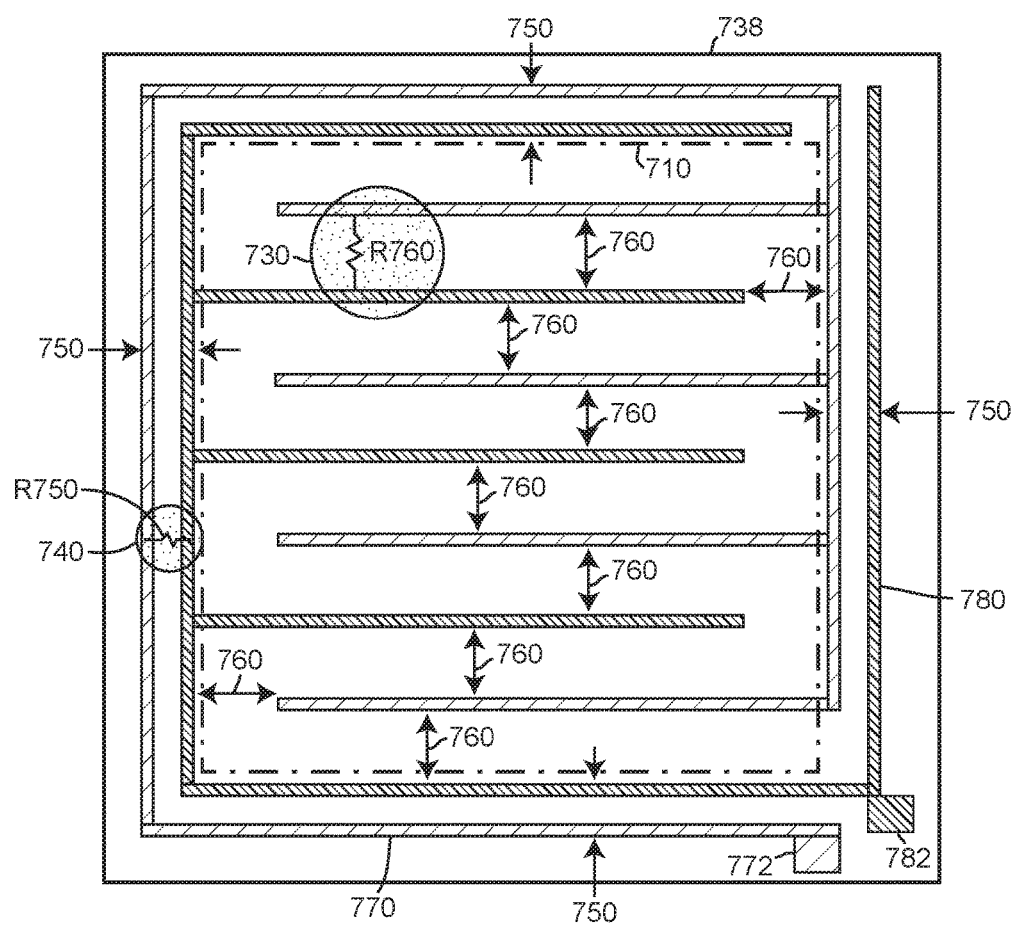

As discussed with respect to FIGS. 2 and 3, an area of spread may relate to a volume of liquid in an absorbent layer, so a range of spread of a liquid, as discussed above, may relate to a range of volumes of liquid in an absorbent layer.

At the boundary, the range of the spread of liquid is represented by the diameter of liquid 440 and 444. Depending on where the liquid is introduced with respect to the boundary (e.g., 442, 446), a liquid may spread a distance of 450 (e.g., liquid 440) before the liquid spreads between conductors 470 and 480 or a distance less than distance 460 (e.g., liquid 444) before the liquid contacts conductors 470 and 480 thereby creating a circuit at the boundary.

The existence of an electrical circuit between conductors 470 and 480 indicates that there is a liquid between conductors 470 and 480 along boundary 410 or between conductors 470 and 480 within boundary 410. The layout of conductors 470 and 480 in implementation 400-600 prohibits processing circuit 162 from distinguishing whether liquid is at boundary 410 as opposed to within boundary 410 by simply detecting the existence of an electrical circuit.

In an implementation where area 438 is implemented as a pad for a hospital bed, a nurse would want to change the pad if liquid at boundary 410 is about to leak or if the pad holds a minimum volume of liquid represented by liquid 430 or 434. The nurse would not need to receive a notice of liquid that distinguishes between liquid at boundary 410 are a minimum amount of liquid within boundary 410 because in either case, the pad must be changed.

Upon detecting a circuit, processing circuit 162 may provide a notice. The notice for detecting liquid at boundary 410 is the same for detecting liquid inside boundary 410 since processing circuit 162 cannot distinguish between liquid at boundary 410 from liquid within boundary 410 for implementations 400-600 when detecting only the existence of a circuit and not a magnitude of impedance.

Conductors 470 and 480 may include contacts 472 and 482 to facilitate mechanical and/or electrical coupling of determiner 160 to conductors 470 and 480. Contacts 472 and 482 may also couple to an RF circuit (e.g., RFID tag) and determiner 160 may include an RF reader.

As discussed above, a processing circuit may apply a force to a conductor, detect (e.g., measure) a physical characteristic, and perform a calculation using the detected physical characteristics. For example, a processing circuit may apply a voltage to a conductor, measure a current provided via the conductor, and calculate the impedance (e.g., resistance) of the conductor. Detecting the magnitude of the resistance of an inductor may permit a processing circuit to determine whether liquid is located at a boundary or whether liquid is located within the boundary.

In implementation 700 includes conductors 770 and 780. Portions of conductors 770 and 780 are positioned along boundary 710 of area 738. Along the boundary, conductors 770 and 780 are positioned distance 750 away from each other. In one implementation, conductors 770 and 780 are positioned at most distance 750 away from each other along boundary 710. As discussed above with respect to distance 450, distance 750 may relate to the absorbency of an absorbent layer in area 738. Although the distance between conductors 770 and 780 is shown as distance 750 along the entire boundary 710, the distance between conductors 770 and 780 may be different along one or more portions of boundary 710.

The distance between conductors 770 and 780 within boundary 710 is distance 760. In one implementation, the distance between conductors 770 and 780 within boundary 710 is at least (i.e., no less than) distance 760. In this implementation in which the impedance of an electrical circuit may be used to distinguish between liquid at the boundary and liquid within the boundary, distance 760 must be different than distance 750.

When conductors form a circuit to provide a current through a liquid such as urine or blood, the greater the distance between the conductors, the greater the impedance of the circuit. As a result, if distance 760 is different than distance 750, a circuit through liquid at the boundary will have a different impedance than a circuit through liquid inside the boundary.

For example, in implementation 700, distance 760 is greater than distance 750. Assume that the impedance of the entire length of conductor 770 and the entire length of conductor 780 is significantly (e.g., order of magnitude or more) less than the impedance of the liquid. Because the impedance of conductors 770 and 780 are significantly less than the impedance through the liquid, the magnitude of the impedance of a circuit through the liquid will be determined primarily by the impedance of the liquid. Because the distance between conductors 770 and 780 within boundary 710 are spaced farther apart than the distance between conductors 770 and 780 along the boundary, the impedance of a circuit through liquid within the boundary will be greater than the impedance of a circuit through liquid at the boundary.

The difference in impedance of the two circuits may be proportional to the difference in distance 760 and distance 750 for the same liquid.

As discussed with respect to FIGS. 2 and 3, an area of spread may relate to a volume of liquid in an absorbent layer, so a range of spread of a liquid, as discussed above, may relate to a range of volumes of liquid in an absorbent layer.

To detect a liquid, processing circuit 162 applies a voltage between conductors 770 and 780, measures the resulting current, and determines the impedance of the circuit. If little or no current flows, no liquid is present at the boundary or within the boundary. When the impedance of a circuit between conductor 770 and conductor 780 is greater than a threshold, the liquid is positioned within the boundary. When the impedance is less than the threshold, the liquid is positioned at the boundary.

Determining whether the liquid is positioned at the boundary or within the boundary may include more than one impedance threshold. An upper threshold may indicate that the liquid is positioned within the boundary and has spread distance 760 between conductor 770 and conductor 780. A middle threshold may indicate that the liquid is positioned within the boundary and has spread two times distance 760 to span two lengths (e.g., arms) of conductor 770 and/or conductor 780 within boundary 710. The magnitude of the upper threshold is greater than the magnitude of the middle threshold. A lower threshold may indicate that the liquid is positioned at the boundary. The magnitude of the lower threshold is less than the magnitude of the upper threshold and/or middle threshold.

Because the impedance of conductors 770 and 780 is low compared to the impedance through liquid 730 or 740, a circuit through liquid 730 would have an impedance of R760 whereas the impedance of a circuit through liquid 740 would have an impedance of R750. The magnitude of the impedance of R760 is greater that the magnitude of the impedance of R750. Distance 760 and distance 750 may be adjusted (e.g., increased, decreased) with respect to each other to set the values of R760 and R750 for detection and differentiation by processing circuit 162.

Upon detecting an impedance above a threshold, greater than an upper threshold, and/or impedance R760, processing circuit 162 may provide a notice for detecting liquid within boundary 710. Upon detecting an impedance below a threshold, less than a lower threshold, and/or impedance R750, processing circuit 162 may provide a notice for detecting liquid at boundary 710.

Conductors 770 and 780 may include contacts 772 and 782 to facilitate mechanical and/or electrical coupling of determiner 160 to conductors 770 and 780. Contacts 772 and 782 may also couple to an RF circuit (e.g., RFID tag) and determiner 160 may include an RF reader.

In implementation 800 includes conductors 870 and 880. Portions of conductors 870 and 880 are positioned along boundary 810 of area 838. Along the boundary, conductors 870 and 880 are positioned distance 850 away from each other. As discussed above with respect to distance 450, distance 850 may relate to the absorbency of an absorbent layer in area 838. Although the distance between conductors 870 and 880 is shown as distance 850 along the entire boundary 810, the distance between conductors 870 and 880 may be different along one or more portions of boundary 810. The distance between conductors 870 and 880 within boundary 810 is distance 860.

In implementation 800, as with implementation 700, the impedance of an electrical circuit may be used to distinguish between liquid at the boundary and liquid within the boundary; however, unlike implementation 700, distance 760 and distance 750 or the relationship between distance 760 and distance 750 in implementation 800 is not an issue.

In implementation 800, conductors 870 and 880 have a magnitude of impedance that is greater than the impedance of a liquid at the boundary or within the boundary. Further, portions of conductor 870 have a higher impedance per length (e.g., per square) that other portions of conductor 870, and portions of conductor 880 have a higher impedance per length that other portions of conductor 880. Because the impedance of either conductor 870 or 880 is greater than the impedance through liquid 830 or 840, the presence of liquid does not significantly alter (e.g., increase, decrease) the impedance of a circuit through the liquid. The impedance of conductor 870 or 880 or portions thereof provide impedance information for determining whether liquid as at boundary 810 or within boundary 810.

When a circuit through conductors 870 and 880 does not exist, the impedance between conductors 870 and 880 is very high or even infinite. When a circuit does exist between conductors 870 and 880, the impedance of the circuit is proportional to the length of the wire in the circuit and the position of the wire, or portion thereof, in area 838. Liquid between the conductors acts to complete a circuit not to greatly alter the impedance of the circuit as with implementation 700.

Circuits formed along boundary 810 may be more easily distinguished from circuits formed within boundary 810 by making the impedance per unit length (e.g., ohms per square) of the portions of conductors 870 and 880 along the boundary 810 different from the ohms per square of the portions of conductors 870 and 880 within boundary 810.

For example, the width of the portions of conductors 870 and 880 along boundary 810 are depicted as being wider than the width of the portions of conductors 870 and 880 within boundary 810 to portray a lesser ohms per square impedance of conductors 870 and 880 along boundary 810 and a greater ohms per square impedance of conductors 870 and 880 within boundary 810. A circuit having a lower magnitude impedance indicates liquid at boundary 810 while a circuit having a higher magnitude impedance indicates a liquid within boundary 810.

For example, assume that the impedance of the portions of conductors 870 and 880 along the boundary is X ohms per square and the impedance of the portions of conductors 870 and 880 within the boundary is Y ohms per square. In the equations below, the indicators 810, 812, 814, 820, 822, 824, 854, 856, 858, and 862 indicate distances. The impedance of a circuit through liquid 830 is the sum of the lengths, which is:

(810+812+850+854)*X+R860+(856+858)*Y+(862+814)*X.

The impedance of a circuit through liquid 840 is:

(810+812+814)*X+R850+(820+822+834)*X.

As long as the ohms per square of the portions of conductors 870 and 880 within boundary 810 (e.g., distance 856, distance 858) is great enough with respect to the ohms per square of the portions of conductors 870 and 880 along boundary 810 so that any circuit formed within boundary 810 has a greater impedance than any circuit formed at boundary 810 then processing circuit 162 will be able to distinguish between liquid at boundary 810 and liquid within boundary 810.

In an implementation, the dimensions of area 838 are W in width (e.g. distance 852) and L in length (e.g., distance 812). The maximum magnitude of the impedance of the portions of conductors 870 and 880 along boundary 810 is about:

((2*W+2*L)+(2*W+2*L))*(X ohms per square).

Which simplifies to be:

(4*W+4*L)*(X ohms per square).

Figure 8:
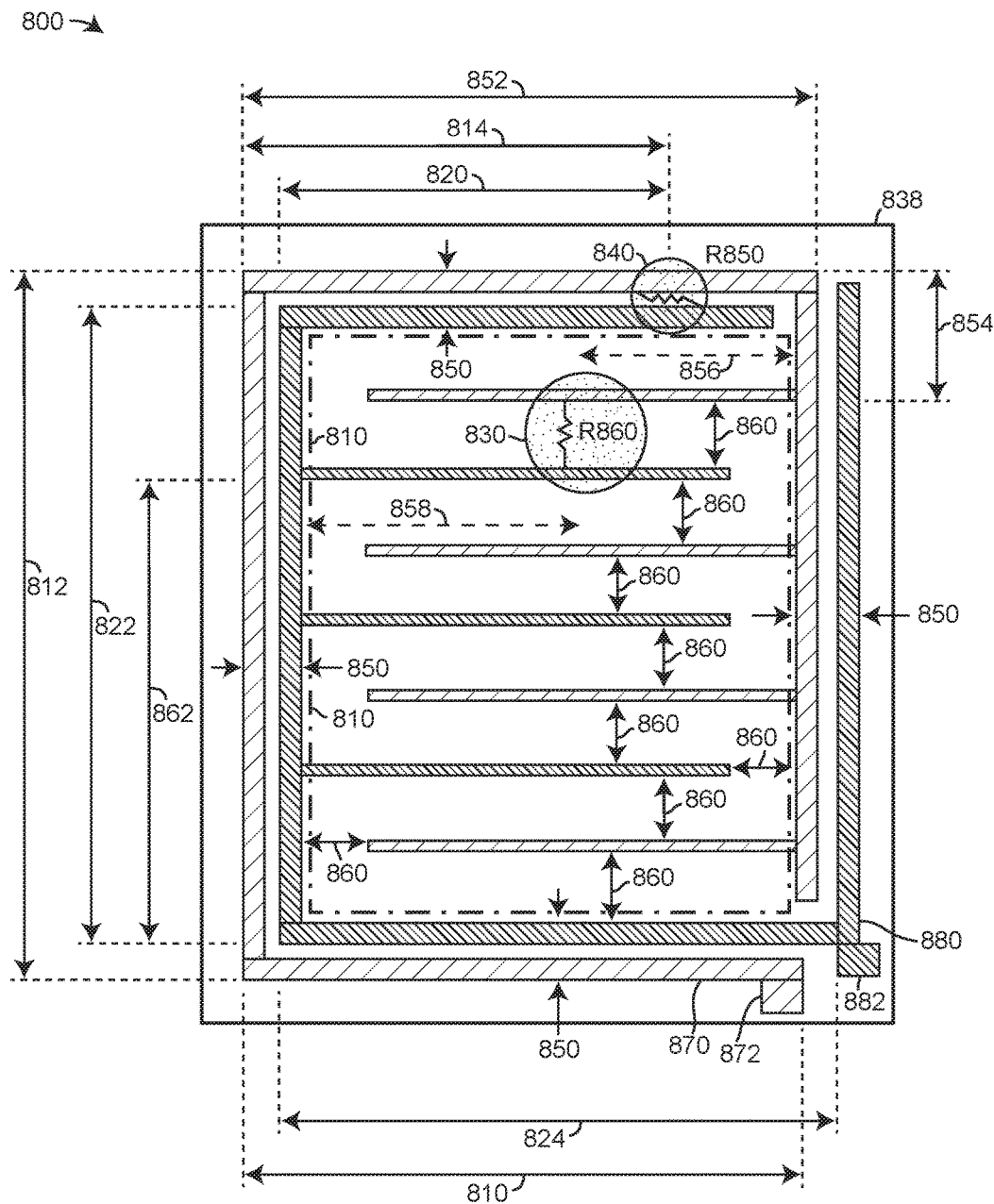

For the layout show in FIG. 8, any circuit within boundary 810 traverses portions of conductors 870 and 880 equivalent in length to width W (e.g., distance 852) of area 838. So, the magnitude of the impedance of the portions of conductors 870 and 880 within boundary 810 is about:

W*(Y ohms per square).

In order for processing circuit 162 to distinguish between liquid at boundary 810 and liquid within boundary 810:

Y>(4W+4L)*(X/W)

If W is about the same length as L, then Y must be about 8 times greater than X for processing circuit 162 to distinguish between liquid at boundary 810 and liquid within boundary 810. When the impedance in ohms per square of the portions of conductors 870 and 880 within boundary 810 is more than at least 15-20 times greater than the impedance in ohms per square of the portions of conductors 870 and 880 along boundary 810 then processing circuit 162 can distinguish between liquid at boundary 810 and liquid within boundary 810.

The impedance of a conductor may be established by the material (e.g., gold, silver, carbon) used to form the conductor or to form a portion of the conductor. The impedance of a conductor may be further established by the structure (e.g., width, thickness) of the conductor to establish an impedance in ohms per square.

In implementation 900, conductors 470 and 480 have a low impedance with respect to the impedance of the liquid, but include a resistance that distinguishes conductor 470 from conductor 480 and conductors 470 and 480 from liquid between conductors 470 and 480.

Any electrical circuit between conductor 470, liquid, and conductor 480 also includes either resistance R970 or resistance R980. The magnitude of the impedance of resistance R970 and/or resistance R980 is greater than the impedance through liquid between conductors 470 and 480 whether the liquid is positioned at the boundary or within the boundary. Resistances R970 and R980 are positioned with respect to conductors 470 and 480 so that any electrical path from contact 472 through conductor 470, liquid (e.g., 440, 444, 430, 434, 920), and conductor 480 to contact 482 includes either R980 or the sum of R970 and R980. Detecting a magnitude of an impedance approximately equal to R980 or the sum or R970 and R980 provides an indication of whether the liquid is at the boundary or within the boundary.

For example, an electrical path through liquid 440, liquid 444 and liquid 920 includes resistance R980. An electrical path through liquid 430 and 434 includes resistance R970 and R980. The magnitude of impedance between conductors 470 and 480 may be compared to a threshold to determine whether the liquid is positioned at the boundary or within the boundary. A threshold may include a magnitude of impedance that is more than the magnitude of the impedance of resistance R980 and less than the sum of the impedance of resistances R970 and R980.

Figure 9:
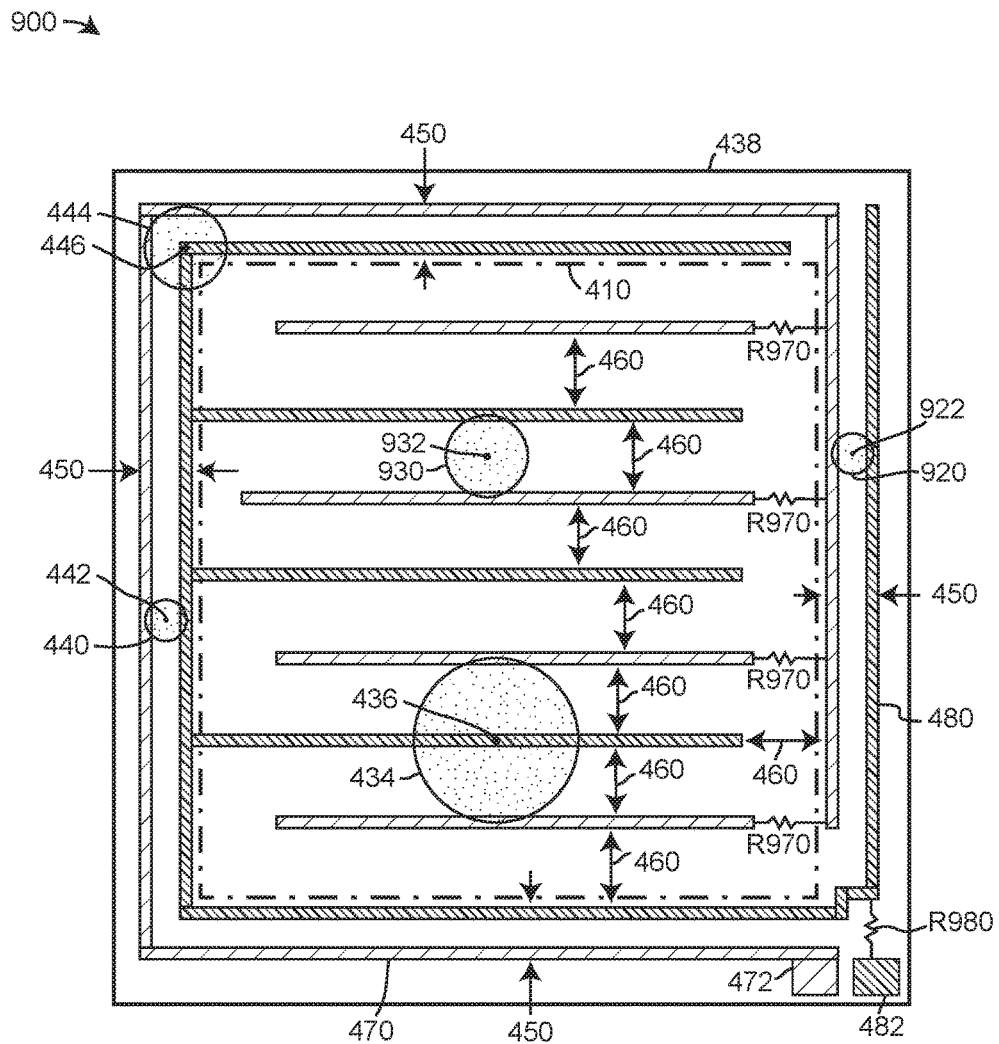

In FIG. 9, resistances R970 and R980 have been added to the conductors of implementation 400. Resistances may be added to any implementation to distinguish liquid at the boundary from liquid within the boundary.

Resistances R970 and R980 may be implement using any conventional material and/or component. Resistances R970 and R980 may be conventional resistors that electrically couple to conductors 470 and 480. Resistances R970 and R980 may be formed of the same material as conductors 470 and/or 480, but have a different impedance per unit (e.g., ohms per square). Resistances R970 and R980 may be formed of a different material than conductors 470 and 480 to provide the impedance of resistances R970 and R980.

The magnitude of the impedance of resistance 980 may be greater than the magnitude of the impedance of the longest electrical path through conductors 470 and 480 along boundary 410 plus the impedance of any liquid (e.g., 440, 444, 920) between conductors 470 and 480 along the boundary so that the magnitude of the impedance of resistance 980 is approximately the impedance of any electrical circuit along the boundary.

The magnitude of the impedance of the sum of resistances R970 and R980 may be greater than the magnitude of the impedance of the longest electrical path through conductors 470 and 480 within boundary 410 plus the impedance of any liquid (e.g., 430, 434) between conductors 470 and 480 within the boundary so that the magnitude of the sum of the impedance of resistances R970 and R980 is approximately the impedance of any electrical circuit within the boundary.

A threshold (e.g., value) for detecting a liquid at boundary 410 may be detecting an impedance approximately equal to the impedance of resistance R980. A threshold for detecting a liquid within boundary 410 may be detecting an impedance approximately equal to the impedance of the sum of resistances R970 and R980. As discussed above, a single threshold may be used so that detecting an impedance less than the threshold indicates liquid at the boundary while detecting an impedance greater than the threshold indicates liquid within the boundary.

Upon detecting an impedance less than a threshold or approximately equal to a lower value, processing circuit 162 may provide a notice of liquid at the boundary. Upon detecting an impedance greater than a threshold or approximately equal to a higher value, processing circuit 162 may provide a notice of liquid within the boundary.

Implementation of a Pad for a Hospital Bed

Prolonged exposure to urine and other liquids is one of the primary causes for bedsores, rashes, and other skin irritation for patients. The cost and labor associated with the treatment of bedsores and other skin conditions is a major issue for hospitals and long-term medical care facilities. The total cost of incontinence care products is less than 2% of a hospital or long-term care facilities operating cost. However, the labor cost associated with incontinence care and the treatment of bedsores and other related skin conditions can exceed 15% of total operating expenses.

Advanced incontinence pads have been designed to wick moisture and liquids away from the patient and capture the liquid in one or more absorbent layers of material. The goal is to keep the patient as dry as possible. Hospital incontinence pads are typically composed of three layers; a non-permeable bottom layer, an absorbent middle layer, and permeable top layer. The permeable top layer top is designed to promote the movement of liquid and moisture away from the patient. The highly absorbent middle layer then retains the liquid.

Advanced incontinence pads from manufacturers such as Covidien, Attends, Tranquility and other manufactures can retain a large amount of liquid (e.g., over 1000 ml). The pads have been designed to reduce the number of times that caregivers are required to change the pad while keeping the patient dry. The absorbent middle layer quickly captures all moisture and creates a dry interface with the patient. As a result, it may be hard for a caregiver to accurately assess when the pad needs to be changed.

A system that detects liquid in the absorbent layer of a pad in a manner that may be correlated to a volume of liquid, as discussed above, helps caregivers to know when it is time to change a pad especially when manual inspection is difficult or inconclusive.

Incontinence conditions in long-term patient care include the following facts: the human bladder can hold between 1.5 and 2.0 liters of liquid; the average person urinates between 4 and 8 times per day and up to 20 times per day if afflicted with an incontinence condition; a typical discharge of urine is between 150 ml and 240 ml; and a maximum discharge of urine may be up to 700 ml.

When a patient is positioned over on a pad on a bed, the patient's body forms a depression in the pad and the bed. The depression in the pad under the patient tends to collect most of any discharged liquids. Because the discharged liquid is located under the patient, it is more difficult for the caregiver to determine the status of the pad and when to change the pad. As the absorbent layer of the pad absorbs the liquid, the absorbent layer changes shape so that the surface of the pad against the patient is no longer substantially flat, but includes bumps (e.g., lumps) so that the pad would likely apply uneven pressure on the patient's body thereby increasing the likelihood that bedsores or skin irritations may develop. Once a pad is wet, the uneven surface of the pad may determine a maximum amount of time a patient may be on the pad to reduce the probability of developing bed sores.

Testing provided information as to the spread of a volume of liquid in a pad. Testing was performed using a product named the Peach model pad produced by Tranquility. The size of the Peach model pad is 76 cm by 91 cm. It is a high absorbency pad that is rated to hold up to 1300 ml. Different amounts of liquid (e.g., 100 ml, 200 ml, 400 ml) were poured slowing into the center of the Peach model pads to simulate discharge from a patient positioned on the pad. The testing showed the spread of the liquid in the pad for each amount of liquid.

Four hundred milliliters of liquid spread in the Peach model pad to cover an area having a diameter of about 36 cm. A rectangle draw around the area of absorption was about 41 cm by 35 cm.

Two hundred milliliters of liquid spread in the Peach model pad to cover an area having a diameter of about 28 cm. A rectangle draw around the area of absorption was about 32 cm by 25 cm.

One hundred milliliters of liquid spread in the Peach model pad to cover an area having a diameter of about 22 cm. A rectangle draw around the area of absorption was about 25 cm by 22 cm.

When hand pressure was applied to the 400 ml and 200 ml test areas, the hand became moist to the touch. Moisture from these areas could be transferred to a patient's skin thereby resulting in skin irritation. When hand pressure was applied to the 100 ml test area, the hand remained dry.

The spread of 400 ml of liquid covered a large portion of the Peach model pad and may result in the discomfort of the patient. The spread of 100 ml of liquid covered only a small portion of the area of the Peach model pad. A caregiver likely would not want to change the pad after a 100 ml discharge.

Further testing using the Peach model pad included pouring 200 ml of liquid about 10 cm from the edge of the pad. In the Peach model pad, the absorbent layer does not extend all the way to the edge of the pad. The top layer and the bottom layer of the pad extend about 2.5 cm beyond the edge of the absorbent layer and are bonded together. The 200 ml of liquid was slowing poured onto the pad about 10 cm away from the edge of the pad and about 7.5 cm from the edge of the absorbent layer.

The 200 ml of liquid nearly immediately spread through the absorbent layer and across the upper and lower layers to the edge of the pad and resulted in the liquid leaking from the pad. The testing showed that liquid would leak from the pad even if a much smaller amount of liquid were used. The testing further highlighted the desirability of conductors that detect liquid at the boundary of an area to detect liquid that may leak from a pad.

A system for detecting a liquid in a hospital pad may be used to detect the amount of liquid in the pad, the area where the liquid is positioned (e.g., center, edge), and whether liquid is exiting the pad. A system that detects liquid in a patient setting may further detect (e.g., measure) the amount of time a patient has been on a wet pad.

In one implementation, a system for detecting liquid in a Peach model pad establishes a boundary 3 cm from the edge of the absorbent material in the pad, which is about 5.5 cm from the edge of the pad. As discussed above, conductors of the system are positioned along the boundary so that a circuit may be formed by liquid positioned along the boundary. Preferably the conductors along the boundary are positioned on the absorbent layer so that the conductors are spaced at most up to 3 cm from each other. Because liquid at the edge of the absorbent layer spreads quickly past the edge of the pad to leak from the pad, one conductor implementation positions a first conductor 3 cm from the edge of the absorbent layer along the boundary and a second conductor at most 2 cm away from the first conductor along the boundary.

Within the boundary of the Peach model pad, conductors are spaced at least 25 cm from each other so that liquid must spread at least 25 cm before it forms a circuit between conductors. The spread of 25 cm relates to between 100 ml and 200 ml of liquid in the pad when a circuit is formed between the conductors.

The conductor implementations discussed above may be used with the Peach model pad to detect liquid within a boundary and at a boundary of the Peach model pad.

The foregoing description discusses preferred embodiments of the present invention, which may be changed or modified without departing from the scope of the present invention as defined in the claims. Examples listed in parentheses may be used in the alternative or in any practical combination. As used in the specification and claims, the words 'comprising', 'comprises', 'including', 'includes', 'having', and 'has' introduce an open ended statement of component structures and/or functions. In the specification and claims, the words 'a' and 'an' are used as indefinite articles meaning 'one or more'. When a descriptive phrase includes a series of nouns and/or adjectives, each successive word is intended to modify the entire combination of words preceding it. For example, a black dog house is intended to mean a house for a black dog. While for the sake of clarity of description, several specific embodiments of the invention have been described, the scope of the invention is intended to be measured by the claims as set forth below. In the claims, the term "provided" is used to definitively identify an object that not a claimed element of the invention but an object that performs the function of a workpiece that cooperates with the claimed invention. For example, in the claim "an apparatus for aiming a provided barrel, the apparatus comprising: a housing, the barrel positioned in the housing", the barrel is not a claimed element of the apparatus, but an object that cooperates with the "housing" of the "apparatus" by being positioned in the "housing". The invention includes any practical combination of the structures and methods disclosed. While for the sake of clarity of description several specifics embodiments of the invention have been described, the scope of the invention is intended to be measured by the claims as set forth below.

What is claimed is:

1. A system for detecting at least one of a liquid in an area and the liquid exiting the area, the system comprising:
   a first conductor; and
   a second conductor; wherein:
      absent the liquid, a magnitude of an impedance between the first conductor and the second conductor is greater than a threshold;
      a first portion of the first conductor and a second portion of the second conductor are positioned along a boundary of the area, the first portion is positioned a first distance from the second portion;
      a third portion of the first conductor and a fourth portion of the second conductor are positioned within the boundary, the third portion is positioned a second distance from the fourth portion; and
      in a presence of the liquid, the magnitude of the impedance between the first conductor and the second conductor is less than the threshold thereby indicating that the liquid is at least one of positioned within the boundary and the liquid is positioned outside the boundary.

2. The system of claim 1 wherein the first distance is less than the second distance.

3. The system of claim 1 further comprising an absorbent layer wherein:
   the area of the absorbent layer is coextensive with the area;
   the first portion is positioned proximate to an edge of the absorbent layer;
   the second portion is positioned proximate to an edge of the absorbent layer; and
   the liquid crossing the boundary indicates the liquid is leaking from the absorbent layer.

4. The system of claim 1 wherein the first distance is significantly less than the second distance.

5. The system of claim 1 wherein the first distance being at least an order of magnitude less than the second distance.

6. The system of claim 1 wherein the first portion, the second portion, the third portion and the fourth portion are positioned in a same plane.

7. The system of claim 1 wherein:
   the first portion and the second portion are positioned in a first plane; and
   the third portion and the fourth portion are positioned in a second plane.

8. The system of claim 1 wherein a magnitude of an impedance of the first conductor and the magnitude of an impedance of the second conductor is less than a magnitude per unit area of an impedance of the liquid.

9. A system for detecting at least one of a liquid in an area and the liquid exiting the area, the system comprising:
   a first conductor;
   a second conductor; wherein;
      a magnitude of an impedance of the first conductor and the magnitude of an impedance of the second conductor is less than a magnitude of an impedance of the liquid;
      a first portion of the first conductor and a second portion of the second conductor are positioned along a boundary of the area, the first portion is positioned at most a first distance from the second portion;
      a third portion of the first conductor and a fourth portion of the second conductor are positioned within the boundary, the third portion is positioned a second distance from the fourth portion;
      detecting a magnitude of an impedance between the first conductor and the second conductor less than a first threshold indicates that at least a portion of the liquid is outside the boundary; and
      detecting the magnitude of the impedance between the first conductor and the second conductor greater than a second threshold indicates that the liquid is positioned within the boundary.

10. The system of claim 9 wherein the first distance is less than the second distance.

11. The system of claim 9 wherein the first threshold is less than the second threshold.

12. The system of claim 9 wherein the first threshold is related to the first distance.

13. The system of claim 9 wherein the second threshold is related to the second distance.

14. The system of claim 9 further comprising a processing circuit, wherein the processing circuit relates the magnitude of the impedance between the first conductor and the second conductor to a chemical composition of the liquid.

15. A system for detecting a liquid, the system comprising:
   a first conductor;
   a second conductor; and
   a processing circuit, the processing circuit electrically couples to the first conductor and the second conductor; wherein;

a magnitude of an impedance of the first conductor and a magnitude of an impedance of the second conductor is less than a magnitude of an impedance per unit area of the liquid;

the first conductor is positioned a first distance away from the second conductor;

the liquid spans the first distance between the first conductor and the second conductor and contacts the first conductor and the second conductor;

the processing circuit:
 determines a magnitude of an impedance of an electrical circuit that includes a portion of the first conductor, a portion of the second conductor, and the liquid;
 compares the magnitude of the impedance to a threshold to detect a presence of the liquid; and
 relates the impedance of the electrical circuit to a chemical composition of the liquid.

16. The system of claim 15 wherein the processing circuit uses stored information to relate the impedance of the electrical circuit to the chemical composition of the liquid.

17. The system of claim 15 wherein the liquid comprises one of urine and blood.

\* \* \* \* \*